US00PP16902P3

(12) United States Plant Patent
Jones

(10) Patent No.: US PP16,902 P3
(45) Date of Patent: Aug. 1, 2006

(54) ***NEMESIA* PLANT NAMED 'PENSKY'**

(50) Latin Name: *Nemesia fruticans*
Varietal Denomination: Pensky

(76) Inventor: Sidney James Jones, Penhow Nurseries. St. Brides, Netherwent Magor, Newport, Gwent NP6 3AU (GB)

( * ) Notice: Subject to any disclaimer, the term of this patent is extended or adjusted under 35 U.S.C. 154(b) by 192 days.

(21) Appl. No.: 10/834,961

(22) Filed: Apr. 30, 2004

(65) Prior Publication Data

US 2005/0076415 P1 Apr. 7, 2005

(30) Foreign Application Priority Data

Oct. 6, 2003 (EP) ..... 2003/1793

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

UPOV–ROM, Plant Variety Database, GTI Jouve Retrieval Software, hit on 'Pensky', 2005/03.*

* cited by examiner

*Primary Examiner*—Anne Marie Grunberg

(57) ABSTRACT

A new and distinct cultivar of *Nemesia* plant named 'Pensky' that is characterized by a compact habit, dense upright spikes of blue-purple flowers and oval shaped green leaves. In combination these characteristics set 'Pensky' apart from all other existing varieties of *Nemesia* known to the inventor.

2 Drawing Sheets

Genus: *Nemesia.*
Species: *fruticans.*
Denomination: Pensky.

BACKGROUND OF THE INVENTION

The present invention relates to a new and distinct cultivar of *Nemesia* plant that will be referred to hereinafter by the cultivar name 'Pensky'.

'Pensky' was discovered by the inventor in 2000 at the inventor's nursery in Netherwent, Wales, United Kingdom. 'Pensky' was first observed on a single plant of the inventor's variety of *Nemesia* named 'Pengoon' (U.S. Plant Pat. No. 14,261) in the form of a naturally occurring branch sport which carried lighter-colored flowers than are typical of 'Pengoon'.

'Pensky' and 'Pengoon' distinguished from other *Nemesias* known to the inventor by their compact habit, upright flower spikes, leaves that are more oval in shape, and with thicker tissue.

When compared with the sport parent *Nemesia* 'Pengoon', 'Pensky' differs only in respect of the color of its flowers and flower parts. In overall appearance, 'Pensky' exhibits soft pale lavender blue flowers whereas 'Pengoon' exhibits mid blue flowers. Upon closer examination, the coloration of the palate of the flower of 'Pensky' is white with a dark blue margin, whereas the coloration of the palate of the flower of 'Pengoon' is red-purple.

'Pensky' was first asexually propagated by the inventor at the inventor's nursery in Netherwent, Wales, United Kingdom in 2000 by direct rooting of the single branch that had been observed. 'Pensky' has subsequently be asexually propagated, using tip and branch cuttings, and has been determined to reproduce true to type in successive generations.

SUMMARY OF THE INVENTION

The following traits have been repeatedly observed and represent the distinguishing characteristics of 'Pensky'. In combination these traits set the new cultivar apart from all other existing varieties of *Nemesia* known to the inventor. 'Pensky' has not been tested under all possible conditions and phenotypic differences may be observed with variations in environmental, climatic, and cultural conditions, however, without any variance in genotype.

1. *Nemesia* 'Pensky' exhibits a compact habit.
2. *Nemesia* 'Pensky' exhibits pale soft lavender-blue flowers.
3. *Nemesia* 'Pensky' exhibits upright flower spikes.
4. *Nemesia* 'Pensky' is floriferous and exhibits large, repeat-flowering heads.
5. *Nemesia* 'Pensky' is hardy to USDA Zone 7.

BRIEF DESCRIPTION OF THE DRAWINGS

The accompanying drawings illustrate the distinguishing traits and overall appearance of the new *Nemesia* cultivar 'Pensky'. The plant photographed is one year old, and has been grown to flowering in a 1 gallon container outdoors in Santa Barbara County, Calif.

The drawing labeled as FIG. 1 illustrates the entire plant.

Figure 1:
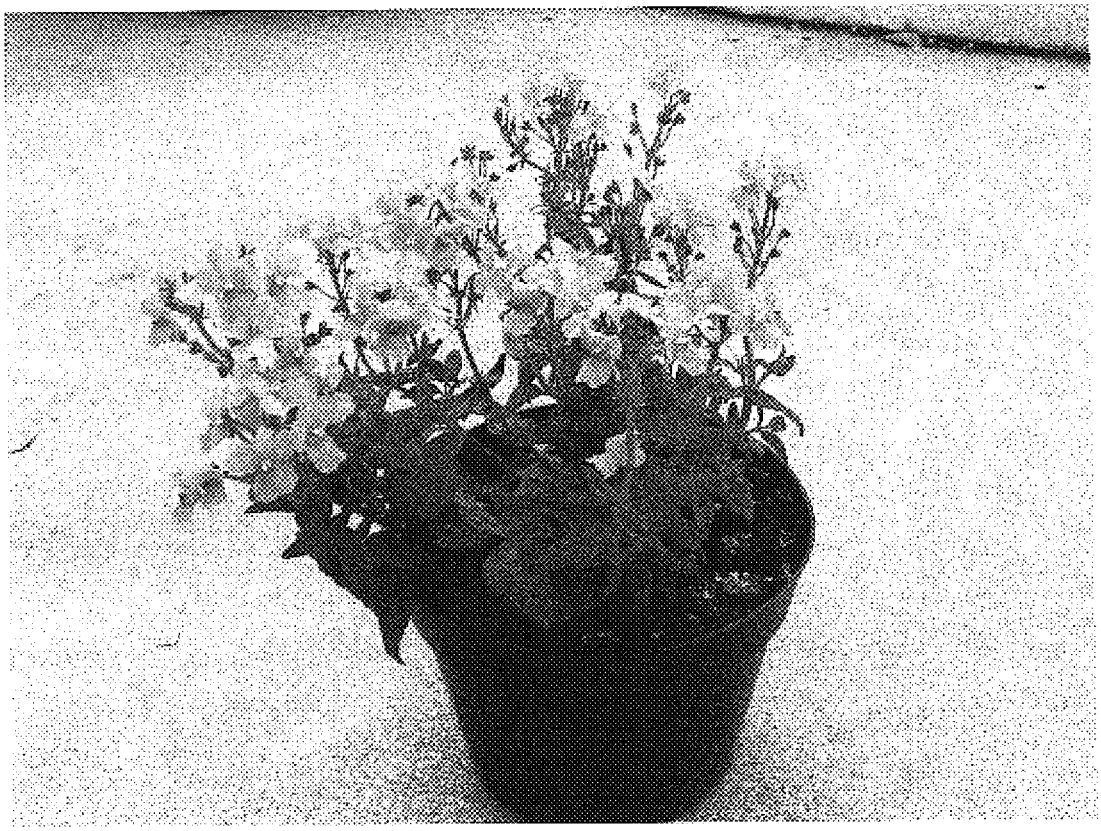
Figure 2:
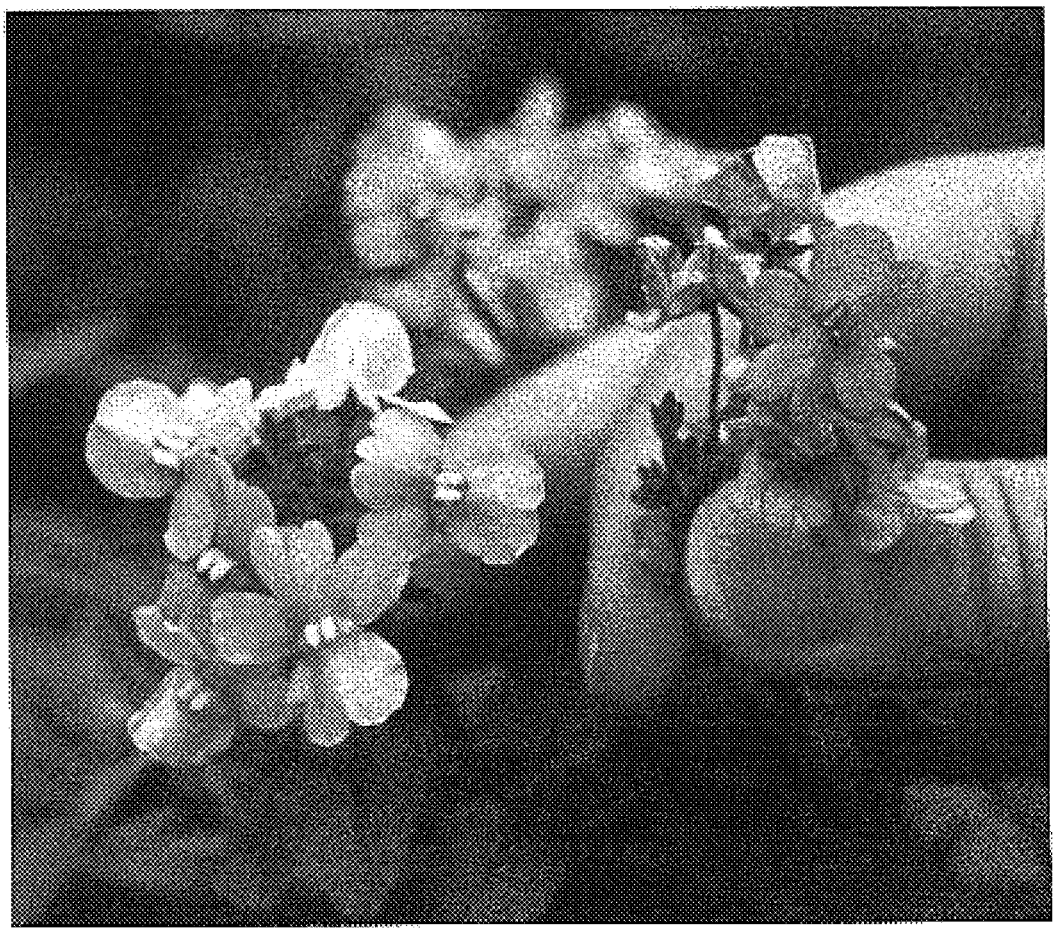

The drawing labeled as FIG. 2 presents, on the left side, a close-up view of the flowers of 'Pensky' and on the right side a hand-held group of flowers taken from a plant of 'Pengoon'. The drawings were made using conventional photographic techniques and the laser copies were made using standard techniques. Although colors may appear different from actual colors due to light reflectance, they are as accurate as possible by conventional photography and laser copying.

BOTANICAL DESCRIPTION OF THE PLANT

The following is a detailed description of the *Nemesia* plant named 'Pensky'. Data was collected in Arroyo Grande, Calif. from plants grown in two-gallon containers under greenhouse conditions. Phenotypic differences may be observed with variations in environmental, climatic, and cultural conditions. The color determinations are in accordance with The Royal Horticultural Society Colour Chart except where general color terms of ordinary dictionary significance are used. The growing requirements are similar to other *Nemesia* plants.

Botanical classification: *Nemesia fruticans* 'Pensky'.
Common name: *Nemesia.*
Use: Bedding and patio plant.
Parentage (sport parent): *Nemesia* 'Pengoon', U.S. Plant Pat. No. 14,261.
Propagation: Vegetative cuttings.
Sexuality: Hermaphrodite.
Growth habit: Compact habit.
Plant dimensions: 36 cm. in height and 64 cm. in width.
Type: Annual or Perennial in USDA Zones 7 and warmer.
Time to initiate roots: Approximately 16 days at temperatures of 21° Centigrade is required to produce rooted cuttings.
Crop time: 12 months are required to produce a finished two-gallon from a rooted cutting.
Pest and disease resistance or susceptibility: In common with *Nemesias* and annual bedding plants generally, Pensky is susceptible to pests including aphids and red spider mites; and diseases including *botrytis* which may result from poor air circulation. Pensky has not been observed to exhibit any particular resistance or susceptibility to pests and diseases.
Root system: Numerous and fine.
Hardiness: Hardy to USDA Zone 7.
Stem:
- *Stem shape.*—Quadrilateral with ridges.
- *Stem length.*—39 cm. in length.
- *Stem diameter.*—3 mm. in diameter.
- *Stem surface.*—Glabrous.
- *Stem color.*—144A.
- *Internode length.*—2 cm–5 cm between nodes.
- *Branching.*—Ascending and freely branching.

Foliage:
- *Leaf shape.*—Ovate.
- *Leaf division.*—Simple.
- *Apex.*—Acute.
- *Base.*—Rounded.
- *Margins.*—Crenulate.
- *Surface.*—Glabrous.
- *Arrangement.*—Opposite.
- *Leaf length.*—2.5 cm. in length.
- *Leaf width.*—1.25 cm. in width.
- *Leaf color* (*adaxial surface*).—137B.
- *Leaf color* (*abaxial surface*).—147B.
- *Attachment.*—Sessile.
- *Vein pattern.*—Parallel.

Flowers:
- *Flowering season.*—Spring and summer.
- *Fragrance.*—Faint perfume fragrance.
- *Self-cleaning or persistent.*—Self-cleaning.
- *Inflorescence dimensions.*—2 cm. in length and 3 cm. in width.
- *Type of inflorescence.*—Axillary raceme.
- *Peduncle dimensions.*—9 mm. in length and 0.50 mm. in diameter.
- *Peduncle surface.*—Stipitate glandular.
- *Peduncle color.*—144A.
- *Bud shape.*—Flattened oval.
- *Bud color.*—62D.
- *Bud dimensions.*—6 mm. in length and 4 mm. in diameter.
- *Flower color.*—76B.
- *Flower shape.*—Personate.
- *Palate color.*—155D outlined in 81B.
- *Nectary* (*located on underside of palate*).—4 mm. in width and 4 mm. in length.
- *Color of nectary.*—1C.
- *Petal surface.*—Glabrous.
- *Petal margin.*—Entire.
- *Petals.*—Four petals in number. Upper lip has four lobes and the lower lip is bilabiate.
- *Petals fused or unfused.*—Basally fused.
- *Flower spur dimensions.*—6 mm. in length and 2 mm. in diameter.
- *Spur color.*—155A.
- *Calyx dimensions.*—3 mm. in height and 6 mm. in width.
- *Sepals.*—Five in number.
- *Sepal surface.*—Stipitate glandular.
- *Sepal apex.*—Acute.
- *Sepal color.*—146A.

Reproductive organs:
- *Stamens.*—Two in number with filaments curved around one another.
- *Color of stamens.*—Between 155A and 155C.
- *Stamen dimensions.*—3 mm. in length and less than 1 mm. in diameter.
- *Anther color.*—161A.
- *Anther dimensions.*—Less than 0.50 mm. in length and less than 0.50 mm. in width.
- *Amount of pollen.*—Moderate.
- *Pistil.*—One.
- *Pistil color.*—155A.
- *Pistil dimensions.*—0.25 mm. in length and 0.25 mm. in diameter.
- *Ovary dimensions.*—0.50 mm. in height and 0.50 mm. in width.
- *Ovary shape.*—Oval to round.
- *Ovary position.*—Superior.
- *Ovary color.*—144B.

Seed production:
- *Quantity of seed.*—Approximately 15 fertile seeds per capsule.
- *Capsules.*—Approximately 20 capsules per flowering spike, but this is markedly influenced by how many times the plant is pinched back.
- *Capsule dimensions.*—5 mm–7 mm in length and 3 mm–5 mm in width.
- *Capsule color.*—177D.
- *Capsule surface.*—Glossy.
- *Appearance of seed.*—Flattened and winged.
- *Seed color.*—200D and wing 156D.
- *Shape of seed.*—Oval.
- *Seed dimensions.*—3 mm. in length and 2.5 mm. in width.

What is claimed is:

1. A new and distinct cultivar of *Nemesia* plant named 'Pensky' as described and illustrated herein.

* * * * *